United States Patent
Ehrenreich et al.

(10) Patent No.: US 8,049,061 B2
(45) Date of Patent: Nov. 1, 2011

(54) EXPANDABLE MEMBER FORMED OF A FIBROUS MATRIX HAVING HYDROGEL POLYMER FOR INTRALUMINAL DRUG DELIVERY

(75) Inventors: Kevin J. Ehrenreich, San Francisco, CA (US); Richard R. Newhauser, Redwood City, CA (US); Randolf von Oepen, Los Altos Hills, CA (US); John Stankus, Campbell, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/238,026

(22) Filed: Sep. 25, 2008

(65) Prior Publication Data

US 2010/0076377 A1    Mar. 25, 2010

(51) Int. Cl.
- *A61F 13/15* (2006.01)
- *A61F 13/20* (2006.01)
- *A61M 31/00* (2006.01)
- *A61M 37/00* (2006.01)
- *A61M 29/00* (2006.01)

(52) U.S. Cl. .................. 604/367; 604/103.08; 604/286; 604/96.01

(58) Field of Classification Search ............. 604/103.08, 604/96.01, 103.06, 101.01, 101.04, 286, 604/365–368
See application file for complete search history.

(56) References Cited

U.S. PATENT DOCUMENTS

| | | |
|---|---|---|
| 4,564,014 A | 1/1986 | Fogarty et al. |
| 4,878,906 A | 11/1989 | Lindemann et al. |
| 4,959,074 A | 9/1990 | Halpern et al. |
| 4,990,357 A | 2/1991 | Karakelle et al. |
| 5,026,607 A | 6/1991 | Kiezulas |
| 5,049,131 A | 9/1991 | Deuss |
| 5,061,273 A | 10/1991 | Yock |
| 5,092,841 A | 3/1992 | Spears |

(Continued)

FOREIGN PATENT DOCUMENTS

DE    10244847    4/2004

(Continued)

OTHER PUBLICATIONS

U.S. Appl. No. 12/237,998, filed Sep. 25, 2008, von Oepen et al.

(Continued)

*Primary Examiner* — Nicholas D Lucchesi
*Assistant Examiner* — Rebecca E Eisenberg
(74) *Attorney, Agent, or Firm* — Randy Shen (57) ABSTRACT

An intraluminal catheter device having an expandable member formed of a matrix of fiber elements, the expandable member including a hydrogel polymer having a therapeutic agent incorporated therein. The hydrogel polymer can be coated on the fiber elements in a co-axial configuration. The fiber elements may also have a second coating including a protective substance surrounding the hydrogel polymer having a therapeutic agent therein. The matrix of fiber elements can be formed by electrospinning. A process of delivering a therapeutic agent to a target site includes providing an intraluminal catheter device having an expandable member formed of a matrix of fiber elements, the expandable member including a hydrogel polymer having a therapeutic agent dispersed therein, and advancing the catheter device at a desired treatment site. Once at the desired treatment site, fluid is introduced into the inflation lumen to expand the expandable member from a first profile to a second profile, and the therapeutic agent is released from the hydrogel polymer and delivered to the desired treatment site.

22 Claims, 4 Drawing Sheets

U.S. PATENT DOCUMENTS

| | | |
|---|---|---|
| 5,102,402 A | 4/1992 | Dror et al. |
| 5,272,012 A | 12/1993 | Opolski |
| 5,295,978 A | 3/1994 | Fan et al. |
| 5,304,121 A | 4/1994 | Sahatjian |
| 5,324,261 A | 6/1994 | Amundson et al. |
| 5,370,614 A | 12/1994 | Amundson et al. |
| 5,380,299 A | 1/1995 | Fearnot et al. |
| 5,456,694 A | 10/1995 | Marin et al. |
| 5,458,573 A | 10/1995 | Summers |
| 5,458,615 A | 10/1995 | Klemm et al. |
| 5,476,476 A | 12/1995 | Hillstead |
| 5,507,768 A | 4/1996 | Lau et al. |
| 5,549,551 A | 8/1996 | Peacock, III et al. |
| 5,562,922 A | 10/1996 | Lambert |
| 5,578,340 A | 11/1996 | Ogawa et al. |
| 5,588,962 A | 12/1996 | Nicholas et al. |
| 5,609,629 A | 3/1997 | Fearnot et al. |
| 5,620,738 A | 4/1997 | Fan et al. |
| 5,674,192 A | 10/1997 | Sahatjian et al. |
| 5,685,847 A | 11/1997 | Barry |
| 5,707,385 A | 1/1998 | Williams |
| 5,728,420 A | 3/1998 | Keogh |
| 5,733,925 A | 3/1998 | Kunz et al. |
| 5,756,144 A | 5/1998 | Wolff et al. |
| 5,766,158 A | 6/1998 | Opolski |
| 5,782,855 A | 7/1998 | Lau et al. |
| 5,820,917 A | 10/1998 | Tuch |
| 5,820,918 A | 10/1998 | Ronan et al. |
| 5,821,343 A | 10/1998 | Keogh |
| 5,824,049 A | 10/1998 | Ragheb et al. |
| 5,837,313 A | 11/1998 | Ding et al. |
| 5,843,033 A | 12/1998 | Ropiak |
| 5,843,089 A | 12/1998 | Sahatjian et al. |
| 5,860,954 A | 1/1999 | Ropiak |
| 5,868,719 A | 2/1999 | Tsukernik |
| 5,891,506 A | 4/1999 | Keogh |
| 5,893,840 A | 4/1999 | Hull et al. |
| 5,900,246 A | 5/1999 | Lambert |
| 5,914,182 A | 6/1999 | Drumheller |
| 5,925,552 A | 7/1999 | Keogh et al. |
| 5,928,916 A | 7/1999 | Keogh |
| 5,945,319 A | 8/1999 | Keogh |
| 5,954,706 A | 9/1999 | Sahatjian |
| 5,977,163 A | 11/1999 | Li et al. |
| 5,980,972 A | 11/1999 | Ding |
| 5,981,568 A | 11/1999 | Kunz et al. |
| 6,010,521 A | 1/2000 | Lee et al. |
| 6,017,741 A | 1/2000 | Keogh |
| 6,033,719 A | 3/2000 | Keogh |
| 6,039,721 A | 3/2000 | Johnson et al. |
| 6,048,620 A | 4/2000 | Zhong |
| 6,050,980 A | 4/2000 | Wilson |
| 6,074,659 A | 6/2000 | Kunz et al. |
| 6,093,463 A | 7/2000 | Thakrar |
| 6,096,726 A | 8/2000 | Opolski |
| 6,099,562 A | 8/2000 | Ding et al. |
| 6,099,926 A | 8/2000 | Thakrar |
| 6,106,889 A | 8/2000 | Beavers et al. |
| 6,107,416 A | 8/2000 | Patnaik et al. |
| 6,110,590 A | 8/2000 | Zarkoob et al. |
| 6,129,705 A | 10/2000 | Grantz |
| 6,143,037 A | 11/2000 | Goldstein et al. |
| 6,146,358 A | 11/2000 | Rowe |
| 6,200,257 B1 | 3/2001 | Winkler |
| 6,214,901 B1 | 4/2001 | Chudzik et al. |
| 6,218,016 B1 | 4/2001 | Tedeschi et al. |
| 6,248,127 B1 | 6/2001 | Shah et al. |
| 6,254,921 B1 | 7/2001 | Chappa et al. |
| 6,264,633 B1 | 7/2001 | Knorig |
| 6,268,390 B1 | 7/2001 | Kunz |
| 6,270,831 B2 | 8/2001 | Kumar et al. |
| 6,280,411 B1 | 8/2001 | Lennox |
| 6,303,179 B1 | 10/2001 | Koulik et al. |
| 6,306,166 B1 | 10/2001 | Barry et al. |
| 6,306,421 B1 | 10/2001 | Kunz et al. |
| 6,335,029 B1 | 1/2002 | Kamath et al. |
| 6,364,856 B1 | 4/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,379,691 B1 | 4/2002 | Tedeschi et al. |
| 6,382,526 B1 | 5/2002 | Reneker et al. |
| 6,395,208 B1 | 5/2002 | Herweck et al. |
| 6,409,716 B1 | 6/2002 | Sahatjian et al. |
| 6,419,692 B1 | 7/2002 | Yang et al. |
| 6,443,942 B2 | 9/2002 | Van Antwerp et al. |
| 6,447,835 B1 | 9/2002 | Wang et al. |
| 6,461,666 B2 | 10/2002 | Park |
| 6,475,434 B1 | 11/2002 | Darouiche |
| 6,491,938 B2 | 12/2002 | Kunz et al. |
| 6,491,965 B1 | 12/2002 | Berry et al. |
| 6,506,408 B1 | 1/2003 | Palasis |
| 6,506,411 B2 | 1/2003 | Hunter et al. |
| 6,515,009 B1 | 2/2003 | Kunz et al. |
| 6,517,888 B1 | 2/2003 | Weber |
| 6,520,425 B1 | 2/2003 | Reneker |
| 6,521,283 B1 | 2/2003 | Yianni |
| 6,524,274 B1 | 2/2003 | Rosenthal et al. |
| 6,537,194 B1 | 3/2003 | Winkler |
| 6,544,221 B1 | 4/2003 | Kokish et al. |
| 6,544,223 B1 | 4/2003 | Kokish |
| 6,544,544 B2 | 4/2003 | Hunter et al. |
| 6,545,097 B2 | 4/2003 | Pinchuk et al. |
| 6,555,157 B1 | 4/2003 | Hossainy |
| 6,555,225 B1 | 4/2003 | Yoshioka et al. |
| 6,571,771 B2 | 6/2003 | Doering et al. |
| 6,579,539 B2 | 6/2003 | Lawson et al. |
| 6,589,546 B2 | 7/2003 | Kamath et al. |
| 6,596,699 B2 | 7/2003 | Zamora et al. |
| 6,616,650 B1 | 9/2003 | Rowe |
| 6,617,142 B2 | 9/2003 | Keogh et al. |
| 6,627,246 B2 | 9/2003 | Mehta et al. |
| 6,638,563 B2 | 10/2003 | McGee et al. |
| 6,641,611 B2 | 11/2003 | Jayaraman |
| 6,645,547 B1 | 11/2003 | Shekalim et al. |
| 6,649,030 B1 | 11/2003 | Tesar |
| 6,656,156 B2 | 12/2003 | Yang et al. |
| 6,663,881 B2 | 12/2003 | Kunz et al. |
| 6,669,980 B2 | 12/2003 | Hansen |
| 6,673,453 B2 | 1/2004 | Beavers et al. |
| 6,676,987 B2 | 1/2004 | Zhong et al. |
| 6,683,062 B2 | 1/2004 | Opolski |
| 6,695,809 B1 | 2/2004 | Lee |
| 6,695,992 B2 | 2/2004 | Reneker |
| 6,706,408 B2 | 3/2004 | Jelle |
| 6,713,119 B2 | 3/2004 | Hossainy et al. |
| 6,719,991 B2 | 4/2004 | Darouiche et al. |
| 6,730,349 B2 | 5/2004 | Schwarz et al. |
| 6,733,819 B2 | 5/2004 | Burkett et al. |
| 6,737,447 B1 | 5/2004 | Smith et al. |
| 6,743,462 B1 | 6/2004 | Pacetti |
| 6,743,463 B2 | 6/2004 | Weber et al. |
| 6,743,521 B2 | 6/2004 | Hubbell et al. |
| 6,753,071 B1 | 6/2004 | Pacetti |
| 6,753,454 B1 | 6/2004 | Mello et al. |
| 6,764,709 B2 | 7/2004 | Flanagan |
| 6,776,771 B2 | 8/2004 | van Moorlegem et al. |
| 6,793,960 B1 | 9/2004 | Michal et al. |
| 6,818,247 B1 | 11/2004 | Chen et al. |
| 6,821,479 B1 | 11/2004 | Smith et al. |
| 6,821,528 B2 | 11/2004 | Scott et al. |
| 6,828,028 B1 | 12/2004 | Fukui et al. |
| 6,830,583 B2 | 12/2004 | Shah et al. |
| 6,833,153 B1 | 12/2004 | Roorda et al. |
| 6,855,366 B2 | 2/2005 | Smith et al. |
| 6,855,770 B2 | 2/2005 | Pinchuk et al. |
| 6,861,088 B2 | 3/2005 | Weber et al. |
| 6,865,810 B2 | 3/2005 | Stinson |
| 6,884,628 B2 | 4/2005 | Hubbell et al. |
| 6,887,270 B2 | 5/2005 | Miller et al. |
| 6,887,510 B2 | 5/2005 | Villareal |
| 6,890,339 B2 | 5/2005 | Sahatjian et al. |
| 6,899,731 B2 | 5/2005 | Li et al. |
| 6,904,310 B2 | 6/2005 | Knapp et al. |
| 6,918,869 B2 | 7/2005 | Shaw et al. |
| 6,918,927 B2 | 7/2005 | Bates et al. |
| 6,919,100 B2 | 7/2005 | Narayanan |

| Patent No. | Date | Name |
|---|---|---|
| 6,921,811 B2 | 7/2005 | Zamora et al. |
| 6,923,996 B2 | 8/2005 | Epstein et al. |
| 6,926,919 B1 | 8/2005 | Hossainy et al. |
| 6,939,320 B2 | 9/2005 | Lennox |
| 6,953,466 B2 | 10/2005 | Palasis et al. |
| 6,954,977 B2 | 10/2005 | Maguire et al. |
| 6,991,617 B2 | 1/2006 | Hektner et al. |
| 6,994,689 B1 | 2/2006 | Zadno Azizi et al. |
| 7,008,667 B2 | 3/2006 | Chudzik et al. |
| 7,014,913 B2 | 3/2006 | Pacetti |
| 7,048,714 B2 | 5/2006 | Richter |
| 7,048,962 B2 | 5/2006 | Shekalim et al. |
| 7,060,051 B2 | 6/2006 | Palasis |
| 7,066,904 B2 | 6/2006 | Rosenthal et al. |
| 7,083,644 B1 | 8/2006 | Moroni |
| 7,087,135 B2 | 8/2006 | Dillon |
| 7,087,263 B2 | 8/2006 | Hossainy et al. |
| 7,105,175 B2 | 9/2006 | Schwarz |
| 7,108,684 B2 | 9/2006 | Farnan |
| 7,115,299 B2 | 10/2006 | Kokish |
| 7,122,356 B2 | 10/2006 | Keogh et al. |
| RE39,438 E | 12/2006 | Shah et al. |
| 7,163,334 B2 | 1/2007 | Chase et al. |
| 7,182,779 B2 | 2/2007 | Acosta et al. |
| 7,198,855 B2 | 4/2007 | Liebmann Vinson et al. |
| 7,201,935 B1 | 4/2007 | Claude et al. |
| 7,208,190 B2 | 4/2007 | Verlee et al. |
| 7,220,491 B2 | 5/2007 | Rouns et al. |
| 7,226,612 B2 | 6/2007 | Sohier et al. |
| 7,241,455 B2 | 7/2007 | Richard |
| 7,241,478 B2 | 7/2007 | McNeish et al. |
| 7,258,891 B2 | 8/2007 | Pacetti et al. |
| 7,267,847 B2 | 9/2007 | Karamuk |
| 7,279,175 B2 | 10/2007 | Chen et al. |
| 7,326,433 B2 | 2/2008 | Stenzel |
| 7,335,391 B1 | 2/2008 | Pacetti |
| 7,345,053 B2 | 3/2008 | Garvey |
| 7,357,940 B2 | 4/2008 | Richard et al. |
| 7,364,585 B2 | 4/2008 | Weber |
| 7,364,768 B2 | 4/2008 | Rypacek et al. |
| 7,381,418 B2 | 6/2008 | Richard |
| 7,387,810 B2 | 6/2008 | Hossainy |
| 7,390,525 B2 | 6/2008 | Epstein et al. |
| 7,398,118 B2 | 7/2008 | Knapp et al. |
| 7,402,172 B2 | 7/2008 | Chin et al. |
| 7,402,329 B2 | 7/2008 | Pacetti et al. |
| 7,407,684 B2 | 8/2008 | Spencer et al. |
| 7,442,402 B2 | 10/2008 | Chudzik et al. |
| 7,445,792 B2 | 11/2008 | Toner et al. |
| 7,449,210 B2 | 11/2008 | Malik et al. |
| 7,455,875 B2 | 11/2008 | Weber et al. |
| 7,459,169 B2 | 12/2008 | Nilsson et al. |
| 7,462,165 B2 | 12/2008 | Ding et al. |
| 7,468,210 B1 | 12/2008 | Zamora |
| 7,470,469 B1 | 12/2008 | Michal et al. |
| 7,476,246 B2 | 1/2009 | Pathak |
| 7,482,034 B2 | 1/2009 | Boulais |
| 7,485,334 B2 | 2/2009 | Kerrigan |
| 2001/0026834 A1 | 10/2001 | Chappa et al. |
| 2002/0084178 A1 | 7/2002 | Dubson et al. |
| 2003/0064965 A1* | 4/2003 | Richter ............ 514/102 |
| 2003/0065355 A1 | 4/2003 | Weber |
| 2003/0077253 A1 | 4/2003 | Palasis |
| 2003/0100829 A1 | 5/2003 | Zhong et al. |
| 2003/0104030 A1* | 6/2003 | Igaki et al. ............ 424/426 |
| 2003/0206960 A1 | 11/2003 | Iversen et al. |
| 2003/0207019 A1 | 11/2003 | Shekalim et al. |
| 2003/0207907 A1 | 11/2003 | Iversen et al. |
| 2003/0236513 A1 | 12/2003 | Schwarz et al. |
| 2003/0236514 A1 | 12/2003 | Schwarz |
| 2004/0018296 A1 | 1/2004 | Castro et al. |
| 2004/0034337 A1 | 2/2004 | Boulais et al. |
| 2004/0043068 A1 | 3/2004 | Tedeschi et al. |
| 2004/0058084 A1 | 3/2004 | Shekalim et al. |
| 2004/0073284 A1 | 4/2004 | Bates et al. |
| 2004/0087984 A1 | 5/2004 | Kupiecki et al. |
| 2004/0098089 A1 | 5/2004 | Weber |
| 2004/0098106 A1 | 5/2004 | Williams et al. |
| 2004/0106987 A1 | 6/2004 | Palasis et al. |
| 2004/0126400 A1 | 7/2004 | Iversen et al. |
| 2004/0224003 A1 | 11/2004 | Schultz |
| 2005/0025802 A1 | 2/2005 | Richard et al. |
| 2005/0025808 A1 | 2/2005 | Herrmann et al. |
| 2005/0027283 A1 | 2/2005 | Richard et al. |
| 2005/0037047 A1 | 2/2005 | Song |
| 2005/0037048 A1 | 2/2005 | Song |
| 2005/0064005 A1 | 3/2005 | Dinh et al. |
| 2005/0090891 A1 | 4/2005 | Sahatjian et al. |
| 2005/0106206 A1 | 5/2005 | Herweck et al. |
| 2005/0113687 A1 | 5/2005 | Herweck et al. |
| 2005/0163954 A1 | 7/2005 | Shaw |
| 2005/0181015 A1 | 8/2005 | Zhong |
| 2005/0182361 A1 | 8/2005 | Lennox |
| 2005/0215722 A1 | 9/2005 | Pinchunk et al. |
| 2005/0220853 A1 | 10/2005 | Dao et al. |
| 2005/0241577 A1 | 11/2005 | Shekalim et al. |
| 2005/0271701 A1 | 12/2005 | Cottone et al. |
| 2005/0278021 A1 | 12/2005 | Bates et al. |
| 2006/0008606 A1 | 1/2006 | Horn et al. |
| 2006/0013853 A1 | 1/2006 | Richard |
| 2006/0013867 A1 | 1/2006 | Richard et al. |
| 2006/0020243 A1 | 1/2006 | Speck et al. |
| 2006/0020331 A1 | 1/2006 | Bates et al. |
| 2006/0030936 A1 | 2/2006 | Weber et al. |
| 2006/0034931 A1 | 2/2006 | Hansen |
| 2006/0043650 A1 | 3/2006 | Hossainy et al. |
| 2006/0051390 A1 | 3/2006 | Schwarz |
| 2006/0073265 A1 | 4/2006 | Teichman et al. |
| 2006/0079836 A1 | 4/2006 | Holman et al. |
| 2006/0083768 A1 | 4/2006 | Labrecque et al. |
| 2006/0085023 A1 | 4/2006 | Davies et al. |
| 2006/0110209 A1 | 5/2006 | Shekalim et al. |
| 2006/0122697 A1 | 6/2006 | Shanley et al. |
| 2006/0153904 A1 | 7/2006 | Smith et al. |
| 2006/0165872 A1 | 7/2006 | Chappa et al. |
| 2006/0167407 A1 | 7/2006 | Weber et al. |
| 2006/0171981 A1 | 8/2006 | Richard et al. |
| 2006/0184112 A1* | 8/2006 | Horn et al. ............ 604/103.08 |
| 2006/0230476 A1 | 10/2006 | Atanasoska et al. |
| 2006/0280858 A1 | 12/2006 | Kokish |
| 2007/0003599 A1 | 1/2007 | Schwarz |
| 2007/0014827 A1 | 1/2007 | Larrick et al. |
| 2007/0048351 A1 | 3/2007 | Lunn |
| 2007/0172509 A1 | 7/2007 | Nguyen et al. |
| 2007/0212386 A1 | 9/2007 | Patravale et al. |
| 2007/0212388 A1 | 9/2007 | Patravale et al. |
| 2007/0212393 A1 | 9/2007 | Patravale et al. |
| 2007/0255206 A1* | 11/2007 | Reneker et al. ............ 604/96.01 |
| 2007/0259017 A1 | 11/2007 | Francis |
| 2007/0298069 A1 | 12/2007 | Bucay Couto et al. |
| 2008/0015500 A1 | 1/2008 | Herweck et al. |
| 2008/0015628 A1 | 1/2008 | Dubrul et al. |
| 2008/0021385 A1 | 1/2008 | Barry et al. |
| 2008/0027531 A1 | 1/2008 | Reneker et al. |
| 2008/0050415 A1 | 2/2008 | Atanasoska et al. |
| 2008/0050418 A1 | 2/2008 | Ranade et al. |
| 2008/0051871 A1 | 2/2008 | Tuch |
| 2008/0051881 A1 | 2/2008 | Feng et al. |
| 2008/0057102 A1 | 3/2008 | Roorda |
| 2008/0085294 A1 | 4/2008 | Freyman et al. |
| 2008/0113081 A1 | 5/2008 | Hossainy et al. |
| 2008/0118544 A1 | 5/2008 | Wang |
| 2008/0124372 A1 | 5/2008 | Hossainy et al. |
| 2008/0146489 A1 | 6/2008 | Pacetti et al. |
| 2008/0181927 A1 | 7/2008 | Zhao |
| 2008/0188825 A1 | 8/2008 | Atanasoska et al. |
| 2008/0188925 A1 | 8/2008 | Zhao |
| 2008/0195079 A1 | 8/2008 | Moore et al. |
| 2008/0206442 A1 | 8/2008 | Shekalim et al. |
| 2008/0234799 A1 | 9/2008 | Acosta et al. |
| 2008/0254297 A1 | 10/2008 | Edelman |
| 2008/0255508 A1 | 10/2008 | Wang |
| 2008/0255509 A1 | 10/2008 | Wang |
| 2008/0255510 A1 | 10/2008 | Wang |
| 2008/0264336 A1 | 10/2008 | Schwarz et al. |
| 2008/0274159 A1 | 11/2008 | Schultz |
| 2009/0011116 A1 | 1/2009 | Herweck et al. |

| | | | |
|---|---|---|---|
| 2009/0299450 A1 | 12/2009 | Johnson et al. | |
| 2010/0076401 A1 | 3/2010 | Von Oepen et al. | |
| 2010/0081992 A1 | 4/2010 | Ehrenreich et al. | |

FOREIGN PATENT DOCUMENTS

| | | |
|---|---|---|
| EP | 372088 | 6/1990 |
| EP | 519063 | 12/1992 |
| EP | 565604 | 10/1993 |
| EP | 689465 | 1/1996 |
| EP | 708671 | 5/1996 |
| EP | 712615 | 5/1996 |
| EP | 797988 | 10/1997 |
| EP | 803257 | 10/1997 |
| EP | 819011 | 1/1998 |
| EP | 826382 | 3/1998 |
| EP | 836429 | 4/1998 |
| EP | 879595 | 11/1998 |
| EP | 920843 | 6/1999 |
| EP | 932399 | 8/1999 |
| EP | 980280 | 2/2000 |
| EP | 992252 | 4/2000 |
| EP | 1007135 | 6/2000 |
| EP | 1035871 | 9/2000 |
| EP | 1037677 | 9/2000 |
| EP | 1079872 | 3/2001 |
| EP | 1140273 | 10/2001 |
| EP | 1150622 | 11/2001 |
| EP | 1159974 | 12/2001 |
| EP | 1165157 | 1/2002 |
| EP | 1220694 | 7/2002 |
| EP | 1330273 | 7/2003 |
| EP | 1339440 | 9/2003 |
| EP | 1341565 | 9/2003 |
| EP | 1343544 | 9/2003 |
| EP | 1383551 | 1/2004 |
| EP | 1447098 | 8/2004 |
| EP | 1462127 | 9/2004 |
| EP | 1539266 | 6/2005 |
| EP | 1539267 | 6/2005 |
| EP | 1562669 | 8/2005 |
| EP | 1575642 | 9/2005 |
| EP | 1610856 | 1/2006 |
| EP | 1663345 | 6/2006 |
| EP | 1666070 | 6/2006 |
| EP | 1677849 | 7/2006 |
| EP | 1683520 | 7/2006 |
| EP | 1691856 | 8/2006 |
| EP | 1695697 | 8/2006 |
| EP | 1735042 | 12/2006 |
| EP | 1750782 | 2/2007 |
| EP | 1762255 | 3/2007 |
| EP | 1800702 | 6/2007 |
| EP | 1804893 | 7/2007 |
| EP | 1832301 | 9/2007 |
| EP | 1842567 | 10/2007 |
| EP | 1857127 | 11/2007 |
| EP | 1952789 | 8/2008 |
| WO | WO9211890 | 7/1992 |
| WO | WO9211895 | 7/1992 |
| WO | WO9211896 | 7/1992 |
| WO | WO9421308 | 9/1994 |
| WO | WO 95/03083 A1 | 2/1995 |
| WO | WO9630064 | 10/1996 |
| WO | WO9639949 | 12/1996 |
| WO | WO9733552 | 9/1997 |
| WO | WO9811828 | 3/1998 |
| WO | WO9831415 | 7/1998 |
| WO | WO9908729 | 2/1999 |
| WO | WO9916500 | 4/1999 |
| WO | WO 99/27968 A2 | 6/1999 |
| WO | WO9929353 | 6/1999 |
| WO | WO9959649 | 11/1999 |
| WO | WO0010552 | 3/2000 |
| WO | WO0021584 | 4/2000 |
| WO | WO0032238 | 6/2000 |
| WO | WO0032267 | 6/2000 |
| WO | WO 00/48645 A2 | 8/2000 |
| WO | WO0045744 | 8/2000 |
| WO | WO 01/26702 A2 | 4/2001 |
| WO | WO0222198 | 3/2002 |
| WO | WO0243786 | 6/2002 |
| WO | WO0247731 | 6/2002 |
| WO | WO03002267 | 1/2003 |
| WO | WO03008005 | 1/2003 |
| WO | WO03045523 | 6/2003 |
| WO | WO03090684 | 11/2003 |
| WO | WO03092741 | 11/2003 |
| WO | WO04000380 | 12/2003 |
| WO | WO04000381 | 12/2003 |
| WO | WO2004006976 | 1/2004 |
| WO | WO2004022124 | 3/2004 |
| WO | WO2004028582 | 4/2004 |
| WO | WO2004028587 | 4/2004 |
| WO | WO2004028610 | 4/2004 |
| WO | WO2004039445 | 5/2004 |
| WO | WO2004043506 | 5/2004 |
| WO | WO2004058320 | 7/2004 |
| WO | WO2004060405 | 7/2004 |
| WO | WO2004075943 | 9/2004 |
| WO | WO 2004/091714 A2 | 10/2004 |
| WO | WO2004098671 | 11/2004 |
| WO | WO2004098697 | 11/2004 |
| WO | WO2005011766 | 2/2005 |
| WO | WO2005011767 | 2/2005 |
| WO | WO2005011768 | 2/2005 |
| WO | WO2005011772 | 2/2005 |
| WO | WO2005016399 | 2/2005 |
| WO | WO2005018501 | 3/2005 |
| WO | WO2005018606 | 3/2005 |
| WO | WO2005027994 | 3/2005 |
| WO | WO2005037339 | 4/2005 |
| WO | WO2005039664 | 5/2005 |
| WO | WO2005046747 | 5/2005 |
| WO | WO2005049021 | 6/2005 |
| WO | WO2005070008 | 8/2005 |
| WO | WO2005072651 | 8/2005 |
| WO | WO 2005/089855 A1 | 9/2005 |
| WO | WO2005079335 | 9/2005 |
| WO | WO2005079339 | 9/2005 |
| WO | WO2005079754 | 9/2005 |
| WO | WO2005097066 | 10/2005 |
| WO | WO2005098955 | 10/2005 |
| WO | WO2005105171 | 11/2005 |
| WO | WO2005115496 | 12/2005 |
| WO | WO2006014604 | 2/2006 |
| WO | WO2006014607 | 2/2006 |
| WO | WO2006020274 | 2/2006 |
| WO | WO2006020644 | 2/2006 |
| WO | WO2006026587 | 3/2006 |
| WO | WO2006029012 | 3/2006 |
| WO | WO2006042260 | 4/2006 |
| WO | WO2006044308 | 4/2006 |
| WO | WO2006083628 | 8/2006 |
| WO | WO2006102359 | 9/2006 |
| WO | WO2006107359 | 10/2006 |
| WO | WO2006108420 | 10/2006 |
| WO | WO2006116014 | 11/2006 |
| WO | WO2006128016 | 11/2006 |
| WO | WO2006133118 | 12/2006 |
| WO | WO2007008729 | 1/2007 |
| WO | WO2007024500 | 3/2007 |
| WO | WO2007030302 | 3/2007 |
| WO | WO2007030669 | 3/2007 |
| WO | WO2007047473 | 4/2007 |
| WO | WO2007047662 | 4/2007 |
| WO | WO2007120323 | 10/2007 |
| WO | WO2007120897 | 10/2007 |
| WO | WO2007127488 | 11/2007 |
| WO | WO2008070996 | 6/2008 |
| WO | WO2008087488 | 7/2008 |
| WO | WO 2008/124310 | 10/2008 |
| WO | WO2009005933 | 1/2009 |
| WO | WO 2010/027998 | 3/2010 |

OTHER PUBLICATIONS

U.S. Appl. No. 12/238,627, filed Sep. 26, 2008, Ehrenreich et al.
Kesting, Robert E., "Phase Inversion Membranes," in Synthetic Polymeric Membranes, 2nd Ed., Chapter 7, pp. 237-286, 1985.

Tepe et al., "Local Delivery of Paclitaxel to Inhibit Restenosis During Angioplasty of the Leg," N. Engl. J. Med, 358;7, pp. 689-699, Feb. 14, 2008.
Werk et al., "Inhibition of Restenosis in Femoropopliteal Arteries Paclitaxel-Coated Versus Uncoated Balloon: Femoral Paclitaxel Randomized Pilot Trial," Circulation. 2008;118:1358-1365, Sep. 8, 2008.
Non-Final Office Action mailed on Dec. 28, 2009 for U.S. Appl. No. 12/237,998.
Response and Amendment to Non-Final Rejection filed on Mar. 29, 2010 for U.S. Appl. No. 12/237,998.
Final Rejection mailed on Jun. 21, 2010 for U.S. Appl. No. 12/237,998.
Non-Final Rejection mailed on Feb. 8, 2010 for U.S. Appl. No. 12/238,627.
Response and Amendment to Non-Final Rejection filed on May 10, 2010 for U.S. Appl. No. 12/238,627.
Response and Amendment to Final Rejection filed Aug. 23, 2010 for U.S. Appl. No. 12/237,998.
Advisory Action mailed Sep. 7, 2010 for U.S. Appl. No. 12/237,998.
Request for Continued Examination (RCE) filed Sep. 21, 2010 for U.S. Appl. No. 12/237,998.
Final Rejection mailed on Jul. 23, 2010 for U.S. Appl. No. 12/238,627.
Response to Final Rejection filed Sep. 23, 2010 for U.S. Appl. No. 12/238,627.
U.S. Appl. No. 13/069,020, filed Mar. 22, 2011.
Non-Final Rejection mailed Nov. 17, 2010 for U.S. Appl. No. 12/237,998.
Response to non-Final Rejection filed Feb. 17, 2011 for U.S. Appl. No. 12/237,998.
Request for Continued Examination (RCE) filed Oct. 25, 2010 for U.S. Appl. No. 12/238,627.
Non-Final Rejection mailed Dec. 10, 2010 for U.S. Appl. No. 12/238,627.
Response to non-Final Rejection filed Apr. 8, 2011 for U.S. Appl. No. 12/238,627.
U.S. Appl. No. 12/237,998, Apr. 20, 2011 Non-Final Office Action.
U.S. Appl. No. 12/238,627, Jun. 29, 2011 Notice of Allowance.
International Search Report and Written Opinion for PCT/US2011/029327, dated Jun. 21, 2011.

* cited by examiner

Macroscale image of electrospun
PLLA foam conduit (4.0 mm I.D.).

FIG.10

Surface morphology of electrospun PLLA
foam conduit by SEM (scale bar = 10 μm).

FIG.11

EXPANDABLE MEMBER FORMED OF A FIBROUS MATRIX HAVING HYDROGEL POLYMER FOR INTRALUMINAL DRUG DELIVERY

BACKGROUND OF THE INVENTION

1. Field of the Invention

The present invention generally relates to an intraluminal catheter device for use in angioplasty and delivery of a therapeutic agent. Particularly, the present invention is directed to a catheter having an expandable member formed of a matrix of fiber elements and suitable for insertion into the vascular system for delivering a therapeutic agent.

2. Description of Related Art

The systemic administration of therapeutic agents, such as by transoral or intravenous means, treats the body as a whole even though the disease to be treated may be localized. In some cases, systemic administration may not be desirable because the therapeutic agents may have unwanted effects on parts of the body which are not to be treated, or because treatment of the diseased part of the body requires a high concentration of a therapeutic agent that may not be achievable by systemic administration.

It is therefore often desirable to administer therapeutic agents at localized sites within the body. Common examples include cases of localized vascular disease (e.g., heart disease) or diseased body lumens. Among the treatments becoming available for local treatment of vascular disease, are drug-eluting balloons. This type of medical device is typically a percutanueous transluminal coronary angioplasty (PTCA) balloon catheter that carries a therapeutic agent on the surface of the balloon for delivery to the vessel wall. The method generally includes the steps of adding a therapeutic agent to the balloon surface using any of a number of manufacturing processes, such as dip coating, spray coating, painting or pipetting onto the balloon, electron ion deposition, or plasma gamma discharge deposition, inserting the catheter into a blood vessel to a desired location, and expanding the catheter balloon against the surrounding tissue to allow the release of the therapeutic agent.

In these cases, the therapeutic agent disposed on the balloon surface is exposed to the surrounding environment. As a result, it may contact the vascular surface as the device is tracked through the vessel to the treatment site, resulting in loss of the therapeutic agent and a reduced dose of the therapeutic agent to the target site. A further drawback is the premature diffusion of the drug during delivery into the body.

In view of the potential drawbacks to conventional drug delivery techniques, there exists a need for a device and method for the controlled, localized delivery of therapeutic agents to target locations or lesions within a mammalian body, while preventing the premature release or removal of the therapeutic agent during delivery.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a catheter device provided for intraluminal delivery of at least one therapeutic agent within a lumen or by contacting the vessel wall. Particularly, the catheter device includes an elongated catheter shaft having a proximal end portion and distal end portion and an inflation lumen disposed between the proximal end portion and the distal end portion. The catheter device includes an expandable member which is formed of a matrix of fiber elements and is disposed proximate to the distal end of the catheter shaft. The expandable member is formed of a matrix of fiber elements which is configured to define an inner chamber for the expandable member. The fibers are formed from polymers, such as for example, but not limited to, polyamides, polyurethanes, silicone modified polyurethanes, fluoropolymers, polyolefins, polyimides, polyimines, (methyl) acrylic polymers, polyesters, polyglycolide, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly(ε-caprolactone) (PCL), polydioxanone, poly(ethylene glycol) (PEG), poly (vinyl alcohol), and co-polymers thereof.

In accordance with a preferred embodiment of the invention, the matrix of fiber elements are formed by an electrospinning process. Electrospinning is a method based on the ability of an electric field to overcome the surface tension of a polymer or biomacromolecule solution (or melt), and form a conical shape called the Taylor cone. Depending on the solution and process parameters such as polymer concentration, molecular weight, nozzle diameter, charge magnitude, spinning distance, and solution feed rate, continuous fibers can be produced that can have diameters ranging from a few hundred nanometers to several microns.

In accordance with the invention, a hydrogel polymer coating having a at least one therapeutic agent incorporated therein is dispersed on the expandable member. In one embodiment, the hydrogel polymer coating having the therapeutic agent incorporated therein is coated on the individual fiber elements that form the expandable member. Preferably, the hydrogel polymer coating completely surrounds the fiber. Alternatively, the hydrogel polymer coating can partially coat the fiber.

In accordance with yet another embodiment, the expandable member defines an outer surface, and the hydrogel polymer coating with the therapeutic agent incorporated therein is coated on the outer surface of the expandable member. Alternatively, the hydrogel polymer coating incorporating the therapeutic agent can coat both the individual fibers and also the outer expandable member surface. The therapeutic agents include for example, anti-proliferative, anti-inflammatory, antineoplastic, antiplatelet, anti-coagulant, anti-fibrin, anti-thrombotic, antimitotic, antibiotic, antiallergic and antioxidant compounds.

It is contemplated that in an alternative embodiment the expandable member may also be used to deliver angiogenic factors. Growth factors, such as isoforms of vasoendothelial growth factor (VEGF), fibroblast growth factor (FGF, e.g., beta-FGF), Del 1, hypoxia inducing factor (HIF 1-alpha), monocyte chemoattractant protein (MCP-1), nicotine, platelet derived growth factor (PDGF), insulin-like growth factor (HGF), estrogens, folliostatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). In some embodiments, angiogenic factors include, but are not limited to, peptides, such as PR39, PR11, and angiogenin, small molecules, such as PHD inhibitors, or other agents, such as eNOS enhancers.

In accordance with one embodiment of the invention, although incorporation of the therapeutic agent in the hydrogel polymer prevents premature elution of the therapeutic agent during advancement of the catheter device to the desired treatment site, an additional coating of a protective substance can be applied to the coating of hydrogel polymer. In one embodiment, the protective coating is a second coating on the fiber elements, completely or partially surrounding the first coating of the hydrogel polymer having a therapeutic agent incorporated therein. Alternatively, the protective substance coats at least one portion of the hydrogel polymer coating on the outer surface of the expandable member. The protective coating can protect the integrity of the hydrogel polymer coating so it is not damaged as the device is delivered through the anatomy. Additionally, the protective coating further prevents any premature elution of the therapeutic agent from the hydrogel as the device is delivered through the anatomy to the target site. Suitable substances which can be effective as a protective coating include, but are not limited to glucose, hydrophilic coatings, biodegradable materials, substances which are dissolvable in blood or aqueous mediums, or other substances which will crack under expansion and will therefore allow the therapeutic agent to contact the vessel wall.

In accordance with the invention, the intraluminal catheter is used to deliver a therapeutic agent to a desired treatment site. The intraluminal catheter device has an elongated catheter shaft having a proximal end portion and a distal end portion and an inflation lumen disposed between the proximal end portion and the distal end portion. An expandable member that has a therapeutic agent dispersed thereon is disposed proximate to the distal end portion of the catheter. The expandable member is formed of a matrix of fiber elements and includes a hydrogel polymer having a therapeutic agent therein coated on the fiber elements. Additionally or alternatively, the outer surface of the expandable member can be coated with a hydrogel polymer having a therapeutic agent therein. Preferably, the hydrogel polymer is a swellable polymer that incorporates an aqueous solution of a therapeutic agent. The catheter is advanced to a desired treatment site and fluid is introduced into the inflation lumen to expand the expandable member and release the therapeutic agent from the hydrogel polymer and into the vessel wall.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the product and method of the invention. Together with the description, the drawings serve to explain the principles of the invention.

DETAILED DESCRIPTION OF THE PREFERRED EMBODIMENT

Reference will now be made in detail to the present preferred embodiments of the invention. The method and corresponding steps of the invention will be described in conjunction with the detailed description of the intravascular catheter device.

In accordance with the present invention, an intraluminal catheter device is provided for delivery of at least one therapeutic agent within a lumen by contacting the vessel wall. Particularly, the catheter device includes an elongated catheter shaft having a proximal end portion and a distal end portion and an expandable member located proximate to the distal end portion of the catheter shaft, the expandable member constructed of a matrix of fiber elements, the matrix of fiber elements including a hydrogel polymer having a therapeutic agent incorporated therein. In accordance with one embodiment of the invention, the expandable member is fabricated by electrospinning of the fibers into a matrix configuration. Alternatively, the expandable member can be fabricated by melt-blowing or spunbonding processes to create the fibrous matrix.

The expandable member formed from a matrix of fibers contains a hydrogel polymer having a therapeutic agent incorporated therein. The catheter is configured for delivery through an anatomy and to a target treatment site. In accordance with one embodiment of the invention, once positioned near the target treatment site, the expandable member is inflated and the hydrogel is compressed against the tissue or vessel wall. The compression of the hydrogel coating causes the therapeutic agent to be quickly released for transfer into the vasculature and surrounding areas.

Figure 1:
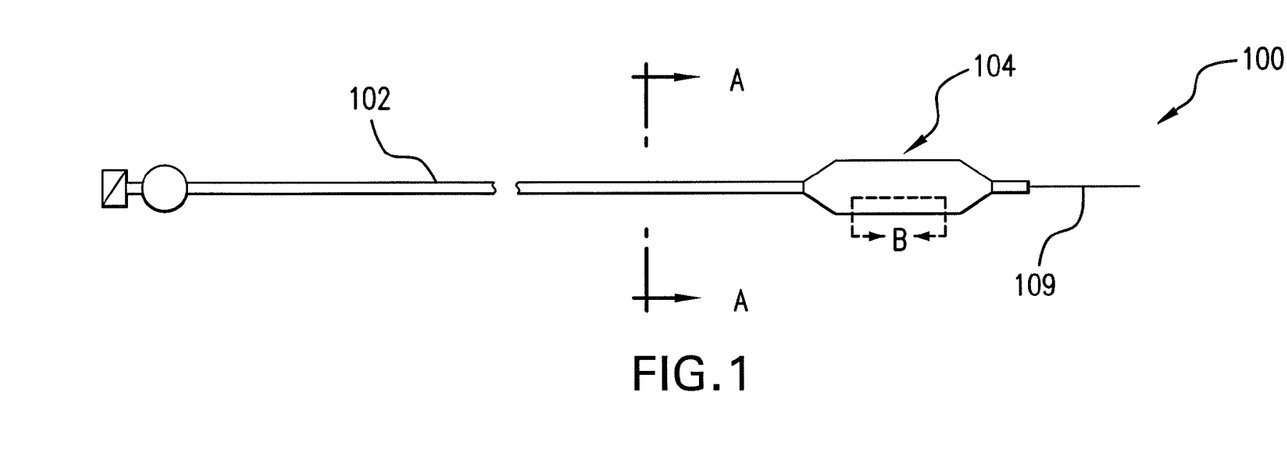
FIG. 1 is a plan view of a catheter having an expandable member constructed of a plurality of fibers and having a hydrogel polymer in accordance with the invention.
Figure 2:
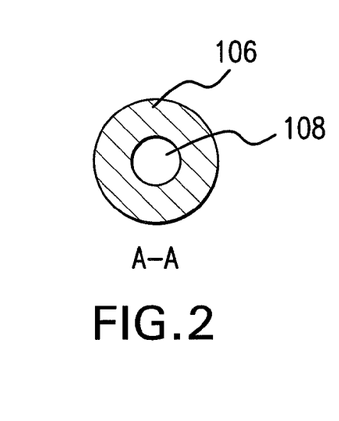
FIG. 2 is a cross-sectional view taken along lines A-A in FIG. 1 in accordance with one embodiment of the present invention.

An exemplary embodiment of the intravascular catheter device in accordance with the present invention is shown schematically in FIGS. 1 and 2, for purpose of illustration only, and not by way of limitation. As shown in FIGS. 1 and 2, the intraluminal medical device 100 generally includes an elongated catheter shaft 102 having a proximal end and having a distal end and an expandable member 104 located proximate to the distal end of the catheter shaft. An inflation lumen 106 can be disposed between the proximal end portion and the distal end portion of the catheter shaft 102. The expandable member 104 is placed in fluid communication with the inflation lumen. The inflation lumen can supply fluid under pressure, and establish negative pressure to the expandable member. The expandable member 104 can thus be inflated and deflated. The elongated catheter is sized and configured for delivery through a tortuous anatomy, and can further include a guidewire lumen 108 that permits it to be delivered over a guidewire 109. The guidewire lumen can have an over-the-wire (OTW) or rapid-exchange (RX) construction, as is well known in the art. Alternatively, the catheter body can include a fixed guidewire to permit the catheter to be delivered to a vessel location without the use of a separate guidewire.

The expandable member is formed of a matrix of fiber elements 110, the expandable member having a hydrogel polymer with at least one therapeutic agent incorporated therein. The matrix configuration allows for a highly accessible surface area of the expandable member. The diameter of the fibers can range from nano to micro in size; preferably from 20 nanometers to 20 micrometers, more preferably from 200 nanometers to 2 micrometers. Accordingly, a vast majority of fibers are required to form an expandable structure configured to be disposed at distal portion of catheter shaft. Further, the fiber elements are configured to achieve a desired thickness of the expandable member. In accordance with a preferred embodiment of the invention, the expandable member thickness ranges from 1 micrometer to 500 microns, and preferably from 5 micrometers to 50 micrometers, based on the fiber size and number of fiber layers deposited.

Figure 3:
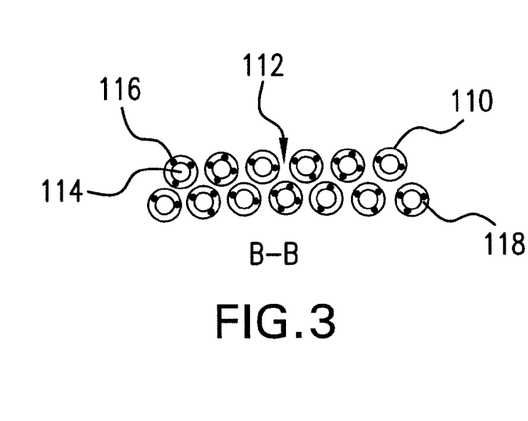
FIG. 3 is a cross-sectional view taken along lines B-B in FIG. 1 in accordance with one embodiment of the present invention.

For purpose of illustration and not limitation as shown in FIG. 3, the polymeric fiber 110 includes a core 114 that is composed of one or more polymeric materials. The polymeric material of the fiber include, but are not limited to, polyamides, polyurethanes, fluoropolymers, polyolefins, polyimides, polyimines, (methyl)acrylic polymers, polyesters, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly(-ε-caprolactone) (PCL), polydioxanone, poly(ethylene glycol) (PEG), poly(vinyl alcohol), and suitable copolymers thereof, poly (ester amides) (PEA), and biodegradable elastomers such as biodegradable poly(ester urethanes) (PEU), polyhydroxyalkanoates such as poly(4-hydroxybutyrate) or poly(3-hydroxybutyrate), poly(1,3-trimethylene carbonate). Alternatively, the core 114 can be a combination of one or more polymeric materials.

In accordance with the invention, the expandable member includes a hydrogel coating having at least one therapeutic agent incorporated therein. In accordance with one embodiment of the invention as illustrated in FIG. 3, the hydrogel polymer coating 118 having at least one therapeutic agent 116 incorporated therein, completely or partially surrounds the polymeric core of the plurality of fibers. Preferably, the hydrogel coating 118 completely surrounds the polymeric core in a co-axial configuration. In this regard, the expandable member 104 is provided with a hydrogel coating 118 including a therapeutic agent 116 for delivery within a vasculature to a targeted area. The matrix and structure provided by the plurality of fibers protects the integrity of the hydrogel coating and therefore can prevent the therapeutic agent from eluting from the hydrogel polymer during the time required to place the device within the vessel lumen and reach the targeted area. Once the target lesion is reached, the member 104 is expanded and the hydrogel polymer 118 having the therapeutic agent 116 incorporated therein is brought into contact with the vessel wall. The hydrogel polymer layer is compressed upon inflation of the expandable member and the therapeutic agent incorporated therein is effectively squeezed out of the hydrogel coating.

In accordance with the invention, as a result of the overlapping matrix configuration of the fiber elements, small gaps 112 are present between the adjacent fibers of the matrix. The diameter of each fiber as well as the configuration of overlapping fibers will affect the gap size of the matrix since it essentially dictates the opening that exists between the fiber elements of the matrix. Processing parameters such as nozzle position and solution composition, among others, can also impact the gap size. The matrix can include gaps of similar or significantly different sizes throughout. In accordance with the invention, the gaps 112 are sized and configured to allow the expandable member to expand from a first profile to a second profile. In this regard, the fibrous matrix is configured to allow the expandable member to easily expand and contact the vessel wall such that the therapeutic agent will be delivered to the vessel wall for treatment of vascular disease. In accordance with one embodiment, the fibrous matrix is configured such that the expandable member is essentially fluid-tight and can maintain an expanded profile for an extended period of time. Alternatively, the fiber matrix is configured such that the expandable member is not necessarily fluid-tight, however the configuration of the fibers allows the expandable member to expand from a first profile to second profile and contact the vessel wall such that the therapeutic agent can be effectively delivered within a lumen by contacting the vessel wall.

Figure 4:
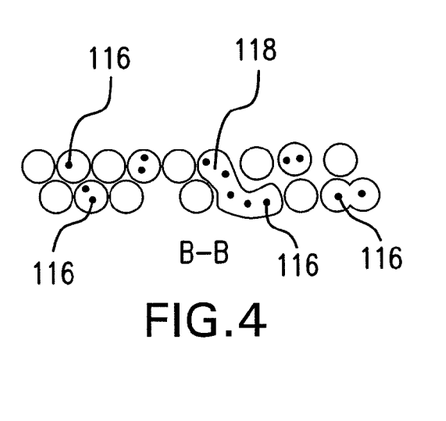
FIG. 4 is a cross-sectional view taken along lines B-B in FIG. 1 in accordance with another embodiment of the present invention.

Additionally or alternatively, as shown in FIG. 4, a hydrogel with a therapeutic agent solution incorporated therein can fill the spaces or gaps between the fibers in the matrix. Incorporating the hydrogel polymer in the spaces or gaps between the fibers in the matrix can assist in the inflation of the expandable member.

Figure 5:
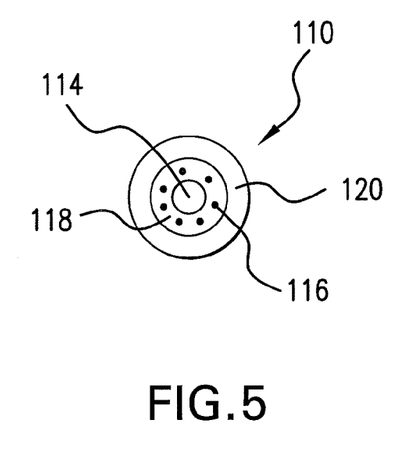
FIG. 5 is a cross-section view of the fiber element of the expandable member in accordance with an alternative embodiment of the present invention.

Although the therapeutic agent is incorporated in the hydrogel polymer to prevent premature elution of the therapeutic agent into the vasculature, an additional protective coating can be applied partially or completely around the hydrogel polymer coating. In an alternative embodiment of the invention, and as illustrated in FIG. 5, the fiber can have a second coating 120 comprising a protective material that can partially or completely surround the hydrogel polymer coating 118 having a therapeutic agent 116 therein. The protective coating 120 can protect the integrity of the hydrogel coating 118 so it is not damaged as the device is delivered through the anatomy. Additionally, the protective coating further prevents any premature elution or release of the therapeutic agent from the hydrogel as the device is delivered through the anatomy to the target site. In accordance with a preferred embodiment of the invention, the protective coating 120 comprises a substance that is dissolvable, biodegradable or disintegrable upon expansion or inflation of the expandable member. For purpose of illustration and not limitation, the protective substance includes glucose, hydrophilic substances, biodegradable substances, contrast mediums, mediums which are dissolvable in blood or aqueous mediums, or other mediums which will crack under expansion and will therefore allow the therapeutic agent to contact the vessel wall. Examples of protective coatings include a water soluble polymer, for example, carbowax, gelatin, polyvinyl alcohol, polyethylene oxide or polyethylene glycol, or a biodegradable or thermally degradable polymer, for example, albumin or pluronic gel F-127. Suitable binders and solvents also can be used to enhance performance of this layer.

Alternatively, the second coating 120 can be a second layer of a hydrogel polymer having a therapeutic agent therein. The hydrogel polymer of the second coating can be different or, alternatively, identical to the hydrogel polymer in the first coating 118. The second coating 120 can also be a layer of a therapeutic agent that is not incorporated in a hydrogel polymer. The therapeutic agent in the second coating 120 can be different or identical to the first therapeutic agent in the first hydrogel polymer coating. This configuration of therapeutic agents in two separate coatings can allow for different release rates of the therapeutic agents.

Figure 6:
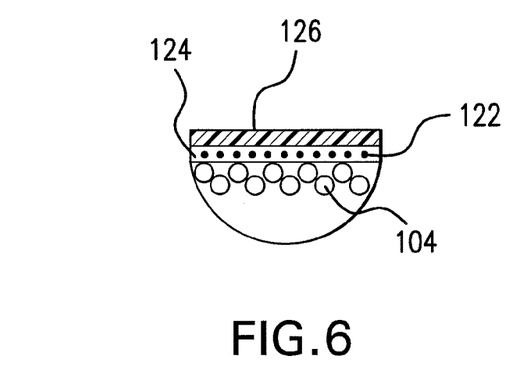
FIG. 6 is a cross-sectional view of the expandable member in accordance with another embodiment of the present invention.

In accordance with a further embodiment of the invention, as illustrated in FIG. 6, the hydrogel polymer 124 having a therapeutic agent 122 therein can be directly applied to the surface of the expandable member 104. The hydrogel polymer coating can be coated over a portion or the entirety of the expandable member 104. In accordance with one aspect of the invention, the hydrogel polymer 124 having a therapeutic agent therein 122 is only present on the surface of the expandable member 104 formed of a matrix of fiber elements. Alternatively, the hydrogel coating having a therapeutic agent therein can be present as both a coating 118 on the fiber elements 110 of the expandable member and as a separate coating 124 on the outer surface of the expandable member 104.

As embodied herein and depicted in FIG. 6, and further in accordance with another aspect of the invention, a protective material 126 can be coated over a portion or the entirety of the inflatable structure 104. As discussed above, the protective material acts as a protective coating for the hydrogel layer having a therapeutic agent therein and, thereby, prevents premature elution of the therapeutic agent prior to proper placement within the vessel lumen at a treatment site and protects the integrity of the hydrogel polymer layer. In accordance with one aspect of the invention, and as depicted in FIG. 6, the protective substance 126 coats the layer of hydrogel polymer 124 having a therapeutic agent incorporated therein. Alternatively, the protective substance can be coated on the outer surface of the expandable member, where the expandable member is formed of a matrix of fiber elements having a hydrogel polymer layer 118 coated on the individual fiber elements 114.

Alternatively, in embodiments where the expandable member is formed of a matrix of fiber elements, the hydrogel polymer layer can be coated on the inner surface of the expandable member. In such an embodiment, the introduction of inflation fluid into the inflation lumen would result in expansion of the expandable member as well as pressure forcing the hydrogel through the fiber matrix. In some of such embodiments the expandable member can be coated on its outer surface with a protective substance In accordance with the invention, the hydrogel coating is characterized by the ability to incorporate a substantial amount of the therapeutic agent, typically in aqueous solution form, and is swellable such that the aqueous therapeutic agent solution can be effectively squeezed out of the hydrogel coating when pressure is applied by inflation of the expandable member. For purpose of illustration and not limitation, the hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides. The hydrogel is a cross-linked polymer material formed from the combination of a colloid and water. Cross-linking reduces solubility and produces a jelly-like polymer that is characterized by the ability to swell and absorb a substantial amount of the therapeutic agent, typically in aqueous solution form. The hydrogel coating is also particularly hydrophilic, water swellable, and lubricious (i.e., having a low coefficient of friction). Preferred hydrogels are polyacrylic acid polymers as described in U.S. Pat. No. 5,091,205 to Fan, incorporated in its entirety by reference herein.

The hydrogel coating is provided on the individual fibers of the expandable member and additionally or alternatively on the outer surface of the expandable member by techniques and methods known to those skilled in the art. For example of illustration and not limitation, the hydrogel coating can be applied by techniques including dip coating, spray coating, transfer by rolling, and additional techniques as understood in the art. The hydrogel coating is swellable such that an aqueous solution of the therapeutic agent can be introduced into the hydrogel polymer coating. The therapeutic agent can be introduced into the hydrogel polymer coating by several techniques and methods known to those skilled in the art. For example, the catheter having a hydrogel polymer adhered to its surface can be immersed into a solution containing the therapeutic agent. Exposure of the hydrogel to the solution causes the aqueous solution to be absorbed into the hydrogel and the hydrogel to subsequently swell. Additionally, the therapeutic agent may be applied in the form of droplets, such as from an eyedropper, or the therapeutic agent may be precipitated into the hydrogel prior to sterilization and sold as a finished device. Methods of producing hydrogel coatings having therapeutic agents therein are disclosed in U.S. Pat. No. 5,954,706 to Sahatjian, the disclosure of which is incorporated in its entirety by reference herein.

In general, when dried, the hydrogel coating should be greater than about 0.5 micrometers in thickness and preferably in the range of about 1.0 to 10.0 micrometers in thickness. The hydrogel coating thickness can swell by about a factor of 1.5 to 10 or even more when the hydrogel is hydrated with a therapeutic solution or aqueous solution. Therefore, the thickness of the hydrated coating is preferably about 1.5 to about 100 micrometers, or more preferably 5 to 50 micrometers in the swelled, uncompressed state.

In accordance with the invention, incorporated in the hydrogel polymer is an aqueous solution of a preselected therapeutic agent to be delivered to the targeted tissue or vasculature. The hydrogel polymer and therapeutic agent are selected to allow for a rapid release of a desired dosage of the therapeutic agent from the hydrogel polymer coating during compression of the hydrogel polymer against the wall of the lumen or by inflation of the expandable device which causes the coating of the hydrogel polymer to decrease in thickness and the therapeutic agent to be released from the hydrogel polymer.

The hydrogel and therapeutic agent combination are preferably noncomplexed, i.e., held together through the ability of the hydrogel to swell and absorb the therapeutic agent solution, thereby allowing the preferable free-release of the therapeutic agent at the desired treatment site. Binding of the therapeutic agent in the hydrogel may also be accomplished by electrostatic attraction of the therapeutic agent to the hydrogel coating, an additive in the hydrogel polymer, or by mechanical binding, e.g., employing a hydrogel coating having a pore size that inhibits inward flow of body fluids or outward flow of the therapeutic itself. Preferably, however, the therapeutic agent is held within the hydrogen-bond matrix formed by the hydrogel polymer.

Figure 7A:
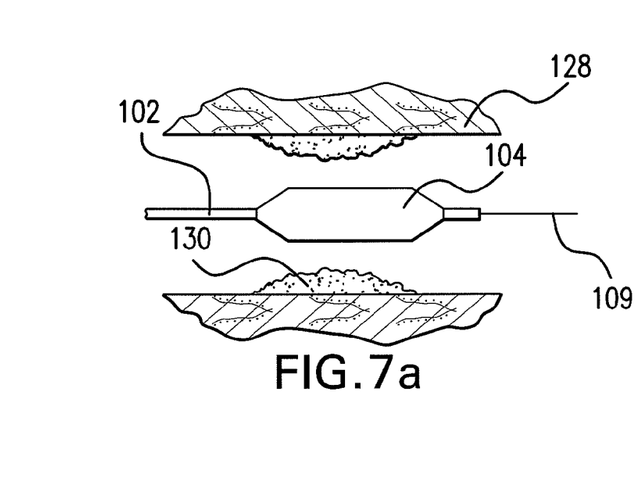
FIGS. 7a and 7b are planar views of a method of use of a catheter having an expandable member constructed of a plurality of fibers having a hydrogel polymer.
Figure 7B:
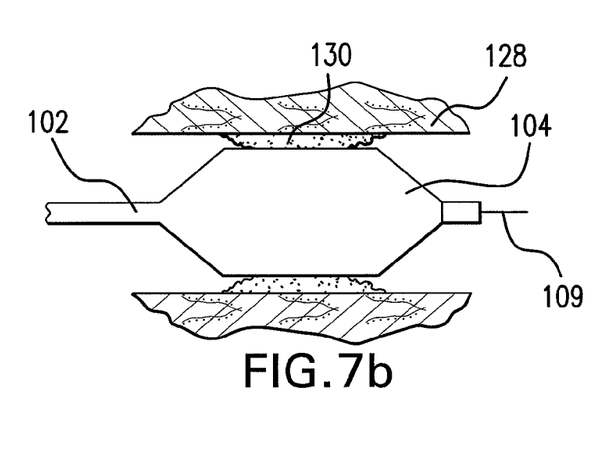

As illustrated in FIGS. 7a and 7b, a method of use is therefore provided in accordance with this invention, the method having the following steps. The expandable portion 104 of the catheter is prepared by introducing an aqueous solution of the therapeutic agent to the hydrogel polymer coating. The catheter is advanced through the vasculature 128 until the expandable member 104 is positioned adjacent to the target disease or desired treatment site 130. Inflation fluid is introduced through the catheter body and into the expandable member 104 to expand or inflate the expandable member. The therapeutic agent can be delivered to the desired treatment site 130 by several techniques. One method of delivering the therapeutic agent includes inflating the expandable member 104 against the vessel wall and compressing the hydrogel such that the therapeutic agent is quickly and freely released into the tissue or vessel wall. The pressure applied to the fluidized therapeutic agent against the tissue or vessel wall by the expandable member during expansion enhances transfer of the therapeutic agent into the tissue or vessel wall. This process is commonly referred to as active diffusion. In accordance with one embodiment, the expandable portion is expanded at pressures sufficient to simultaneously dilate the vessel and deliver the therapeutic agent by compression of the hydrogel polymer coating.

Another method of delivery includes a therapeutic agent release technique, wherein the fibers are expanded or stretched as the expandable member is expanded from a first profile to a second profile and the hydrogel layer is stretched and compressed in thickness causing the therapeutic agent to be squeezed or released from the hydrogel layer and into the surrounding area.

Another method of delivery includes both a diffusion and squeezing mechanism to move the therapeutic agent from the hydrogel layer into the surrounding layers, in accordance with this invention.

In accordance with the invention, the hydrogel polymer is selected to deliver a specific release profile. In accordance with one embodiment, the hydrogel polymer is effective to deliver an initial fast release of the therapeutic agent during initial compression of the hydrogel polymer layer and a slow release of the therapeutic agent remaining in the compressed coating after further inflation of the expandable member. An advantage of incorporating the therapeutic agent in a hydrogel polymer is that large amounts of the therapeutic agent, such as, for example, greater than 20%, even 30-50% or more, of the therapeutic agent contained in the hydrogel, is diffused into the affected area in the short time duration in which the hydrogel is compressed, e.g., 1 second to 5 minutes after the expandable member is inflated at the treatment site. In accordance with the invention, the hydrogel composition and therapeutic agent may be chosen for the purpose of a particular rate-of-release response characteristic, this being dependent on the hydrogel's degree of cross-linking, charge, structure, thickness, or sensitivity to compression, and the therapeutic agent's solubility, particle size and charge.

Accordingly, transporting the therapeutic agent in the hydrogel prevents substantial release of the therapeutic agent to body fluids prior to reaching the treatment area and allows large dosages to be delivered at a desired treatment site during the therapeutic agent application phase. Other factors affecting the dosage are the concentration of the therapeutic agent in the solution applied to the coating and the therapeutic agent-releasability of the hydrogel coating, determined by, for example, the thickness of the hydrogel coating, its resiliency, porosity and the ability of the hydrogel coating to retain the therapeutic agent, e.g., electrostatic binding or pore size, or the ionic strength of the coating, e.g., changed by changing the pH.

In accordance with a further embodiment, the hydrogel coating can partially remain at the vessel wall upon delivery for a more sustained delivery of therapeutic agent. In this regard, the hydrogel polymer is selected to separate from the expandable member and coat the wall of the vessel. In this embodiment, the hydrogel polymer may be soluble in the blood and bioabsorbable. The hydrogel polymer produces a coating on the wall of the vessel and releases the therapeutic agent to the tissue or vessel wall over time as the polymer dissolves.

The therapeutic agent can be delivered from the expandable member by introducing inflation fluid through the catheter body and into the expandable member. Once pressure builds within the expandable member it inflates or expands. The expandable member is configured to provide a radial force against the vessel wall during expansion. In one embodiment, the expansion allows the expandable member to contact the vessel wall and the therapeutic agent to be released from the hydrogel polymer coating and delivered into the vessel wall at the target treatment site. This radial force ensures that the expandable member can expand safely, without causing harm to the vessel wall. Additionally, reducing the stress in the vessel wall can also contribute to a higher rate of uptake of therapeutic agent within the vessel wall as well as improved retention of the therapeutic agent after the catheter has been delivered and removed. The controlled expansion force can be achieved by selecting the appropriate property of the matrix of fiber elements, such as, for example, modulus, gap size, porosity, fiber cross-sectional area or fiber packing density.

For example and not limitation, at least one therapeutic agent can include anti-proliferative, anti-inflammatory, anti-neoplastic, antiplatelet, anti-coagulant, anti-fibrin, anti-thrombotic, antimitotic, antibiotic, antiallergic and antioxidant compounds. As discussed above, the hydrogel polymer and therapeutic agent are selected to allow for a specific release profile from the hydrogel polymer. The therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibodie, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that may be developed in the future for use with intraluminal catheter devices may likewise be used and all are within the scope of this invention.

For example and not limitation, the therapeutic agents effective in preventing restenosis, including those classified into the categories of anti-proliferative agents, anti-platelet agents, anti-inflammatory agents, anti-thrombotic agents, and thrombolytic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIbIIIa or avb3, antibodies that block binding to gpIIaIIIb or avb3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agent. Non-limiting examples of anti-inflammatory agents include prednisone, dexamethasone, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, including, for example, anti-factor VII/VIIa antibodies, rNAPc2, and tissue factor pathway inhibitor (TFPI).

Thrombolytic agents, which can be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other therapeutic agents include cytotoxic drugs, including, for example, apoptosis inducers, including TGF, and topoisomerase inhibitors, including, 10-hydroxycamptothecin, irinotecan, and doxorubicin. Other therapeutic agents include drugs that inhibit cell de-differentiation and cytostatic drugs. The at least one therapeutic agent can also include anti-lipaedemic agents, including fenofibrate, matrix metalloproteinase inhibitors, including, for example, batimistat, antagonists of the endothelin-A receptor, including, for example, darusentan, and antagonists of the avb3 integrin receptor.

Any suitable process for forming an expandable member from a matrix of fiber elements can be used in accordance with the present invention. As discussed above, the expandable member is a shaped structure formed from many fibers that exist in a matrix configuration. As a result of the matrix-like configuration which is tightly woven and overlapped, the expandable member can be expanded with a pressurizing or inflation fluid. Suitable processes for creating the fibrous matrix which is formed into an expandable member include, for example, electrospinning, melt-blowing or spunbonding.

In accordance with a preferred embodiment of the invention, the expandable member is formed by an electrospinning process. Due to the wide variety of materials that can be used for the electrospinning process, the expandable member can be formed from a relatively soft material, which will improve deliverability of the device, and prevent damage to the anatomy during delivery. Additionally, the electrospinning process allows for the fibers to be formed with one or more coatings. In accordance with one embodiment, and as discussed above, the fibers include a base material that supplies structure to the expandable member, and a first coating formed from one or more hydrogel polymers incorporating at least one therapeutic agent. It is also possible to provide a second coating placed over the hydrogel polymer on the electrospun fibers. The second coating can be a protective coating that is dissolvable or disintegrable upon inflation of the expandable member.

Figure 8:
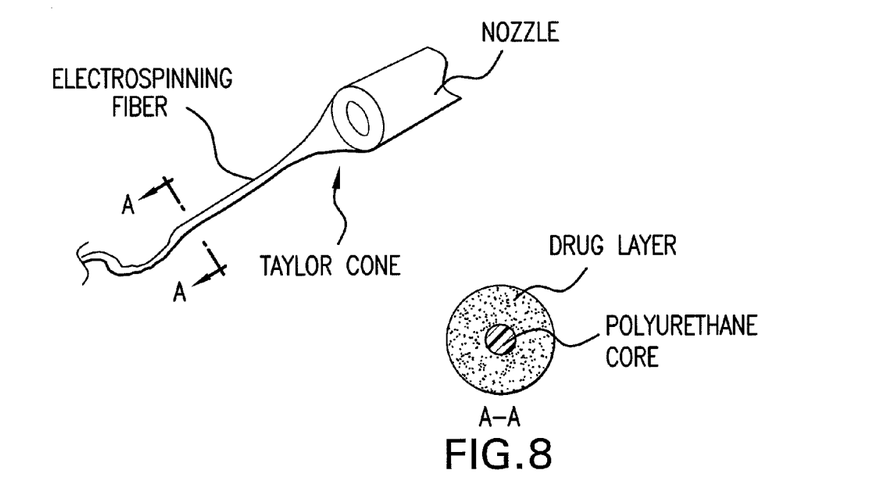
FIGS. 8 and 9 are schematic drawings of an exemplary electrospinning process used to form the expandable member of the present invention.
Figure 9:
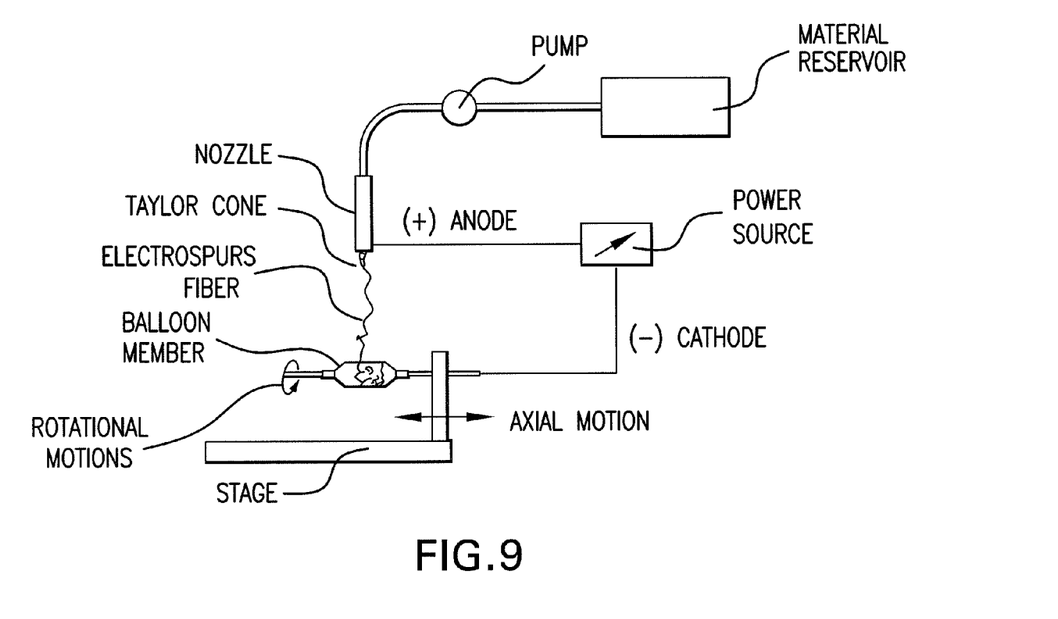
Figure 10:
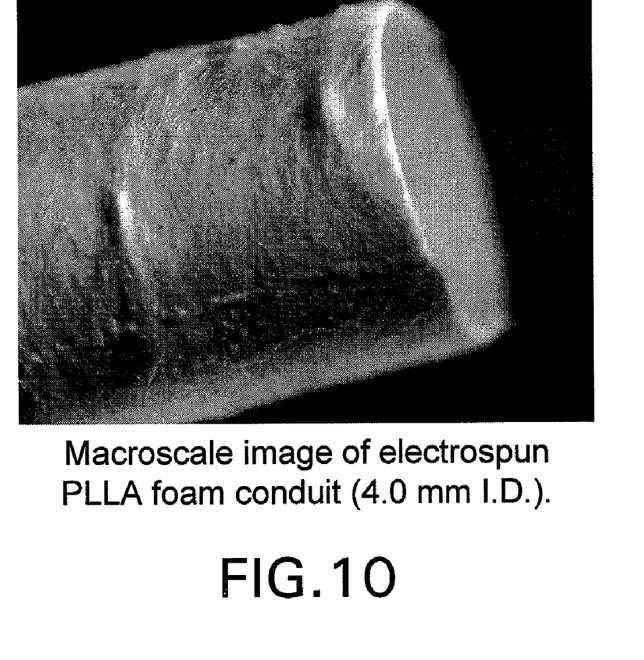
FIGS. 10 and 11 are images of an electrospun foam conduit formed in accordance with the present invention.
Figure 11:
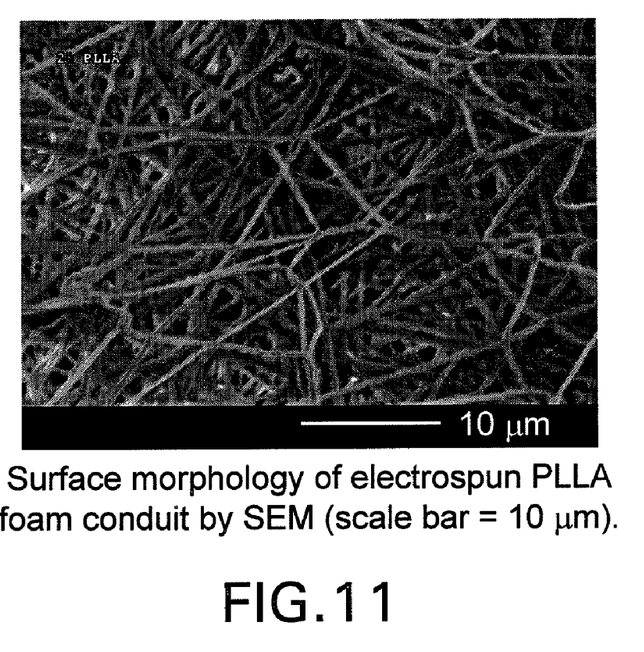

In accordance with a preferred embodiment of the present invention, and as illustrated in FIGS. 8 and 9, for purposes of illustration and not limitation, a method of electrospinning an inflatable member is provided. The process in forming an expandable member, such as a balloon, includes providing a forming mandrel with a profile that is approximately the same as the desired expandable member profile. Material fibers are electrospun onto the mandrel surface. For example, and not limitation, the electrospun fibers are formed from polyurethane dissolved in a solvent such as acetone, tetrahydrofuran, N,N-dimethylformamide, chloroform, trifluoroethanol, hexafluoroisopropanol, or blends thereof. During the electrospinning process, the solvent begins to evaporate. When the electrospinning fibers reach the mandrel surface, the remainder of the solvent evaporates leaving the electrospun fibers. As the electrospinning layers are added, additional crossing of the electrospinning fibers will result in a dense matrix of material having radial channels or gaps passing therethrough. The size and location of these channels and gaps can be controlled through various process parameters, such as solution composition, nozzle position, and other parameters known in the art.

For example, U.S. Pat. Nos. 6,382,526 and 6,520,425, the disclosures of which are incorporated in their entirety by reference herein, are directed to a process and apparatus for the production of nanofibers. An electrospinning fixture is provided that includes a working stage for holding the mandrel that the electrospun material matrix will be formed on. This stage should include rotational and axial movement capabilities and the motion of the stage is to be controlled by a motor synchronized with a motor controller. The stage includes a holding fixture such as a chuck that accepts the balloon member and transmits motion thereto. The holding fixture is also connected to the negative lead of a power source, making it the cathode of the electrolytic process. The positive lead of a power source is connected to the ejection nozzle, making the nozzle the anode of the electrolytic process.

Typically, electrospinning processes require high voltage but relatively low current. In one embodiment of this invention, the power source is capable of delivering 0 to 60 kilovolts of electrical potential, but generally operates in the range of 10 to 20 kilovolts during the electrospinning process. The current that is provided by the power source is generally in the 5 to 10 microampere range. It will be appreciated that these ranges can vary depending upon the electrospinning material and process parameters. Also, it can be preferable to utilize two power sources placed in parallel or in series, depending on the goals of the process.

The nozzle is connected to a reservoir filled with electrospinning material dissolved in a solvent, and is placed in fluid communication with the reservoir by a fluid transport lumen and a pump. The electrospinning material includes thermoplastic polymeric material discussed above in connection with the material of the expandable member. Suitable organic or aqueous based electrospinning solvents, include but are not limited to, acetone, methyl ethyl ketone, cyclohexanone, dichloromethane, chloroform, trifluoroethanol, hexafluoroisopropanol, tetrahydrofuran, N,N-dimethylformamide, ethyl acetate, isopropanol, ethanol, water or blends thereof. A particular embodiment of electrospinning material includes polyurethane dissolved in tetrahydrofuran, although this can be varied widely depending upon the requirements of the invention.

The nozzle can be located in a position that creates the desired electrospinning pattern. For example, if a random matrix pattern is desirable, the nozzle exit can be located greater than about 3 mm from the expandable member surface. If a more controlled pattern is desired, the nozzle can be located within about 3 mm from the expandable member surface. The nozzle exit inner diameter will typically be in the range of about 500 micrometer to 1.5 mm in order to achieve the desired electrospinning fiber size.

The electrospinning fiber will normally be ejected from the Taylor cone adjacent to the anode toward the cathode. The fibers will preferably have diameters in the range of about 20 nanometer to 10 micrometer. This size range will affect the gap size of the matrix since it will determine how much gap exists between overlapping fibers. The density of the fibers and the number of fiber layers will also affect the gap size. It is important to note that various changes to the electrospinning fibers can be made in accordance with this invention, which will affect the efficacy of the solution. For example, it is possible to electrospin a fiber that has two layers, a core (inner layer) and an outer coating (outer layer), by utilizing a specific capillary nozzle, as shown in FIG. 8. This construction will form an electrospinning fiber that has, for example, a polyurethane core and a hydrogel polymer outer coating. Likewise, a second coating (third layer) can be simultaneously spun, which can be a protective coating dissolvable in a solvent. Alternatively, electrospun fiber can have a therapeutic agent core and a polymer outer layer or coating.

In accordance with yet another embodiment, the fibers are spun into single layer strands having a hydrogel polymer dispersed throughout the polymeric fiber. During the electrospinning process, the hydrogel polymer is mixed in the same solution as the solvent and the polymer of the fiber. The solution is then sprayed from a single opening nozzle to form fiber strands having a homogeneous or phase separated distribution of a hydrogel polymer in the polymeric fiber. The fibers can then be dipped in an aqueous solution containing a therapeutic agent and the solution can be absorbed by the hydrogel polymer dispersed throughout the polymeric fiber. As an additional embodiment, the therapeutic agent may also be a part of the electrospinning solution so that additional loading steps would not be required.

To maximize fiber bonding and minimize layer delamination within the electrospun expandable member, fabrication distance can be lowered to an appropriate value to cause fibers to lightly bond between layers due to presence of more solvent with less evaporation distance. As is well know in the art, a shorter process distance results in wetter fibers and tighter junctions.

Further process variables such as polymer solution concentration as stated previously can also affect both morphology and fiber diameter. Increasing polymer concentration and solution viscosity while holding all other variables constant generally results in larger fiber diameter. Fiber diameters can then be varied from tens of nanometers to greater than a micron based on the parameters used. Wall thickness of the nanofiber expandable member could be controlled from tens of microns up to a millimeter or greater by adjusting fabrication time from a few minutes up to an hour or more. Fabrication parameters and material composition can also be optimized for each particular catheter delivery system, to allow for the desired radial force, flexibility and recoverability.

In accordance with another embodiment, the fibrous matrix which is formed into an expandable balloon is formed from a melt-blowing or spunbonding process. The melt blowing process is well known in the art and involves extruding a fiber-forming thermoplastic polymer resin in molten form through orifices of a heated nozzle into a stream of hot gas to attenuate the molten resin as fibers which form a fiber stream, the fibers being collected on a receiver in the path of the fiber stream to form a nonwoven web. The fibrous web can then be shaped into an expandable member. A method for producing a melt-blown fibrous web is described in U.S. Pat. No. 3,978,185 to Buntin et al., which is incorporated herein by reference in its entirety. The spunbonding process, equally well know in the art, is similar to the melt-blowing process, the two major differences between the two processes being i) the temperature and volume of the air used to attenuate the filaments and ii) the location where the filament draw or attenuation force is applied. A melt-blowing process uses large amounts of high-temperature air to attenuate the filaments. The air temperature is typically equal to or slightly greater than the melt temperature of the polymer. In contrast, the spunbonding process generally uses a smaller volume of air close to ambient temperature to first quench the fibers and then to attenuate the fibers. Methods for producing spunbonded webs are disclosed in U.S. Pat. No. 3,338,992 and U.S. Pat. No. 3,341,394 to Kinney; U.S. Pat. No. 3,276,944 to Levy; U.S. Pat. No. 3,502,538 to Peterson; U.S. Pat. Nos. 3,502,763 and 3,509,009 to Hartmann; U.S. Pat. No. 3,542,615 to Dobo et al. and U.S. Pat. No. 3,692,618 to Dorschner et al, the disclosures of which are incorporated herein by reference in their entirety. Both the melt-blowing and spunbonding processes can be used to produce fibers having a diameter of about 100 nanometers. Polymers that are suitable for use in the melt-blowing and spunbonding processes which can be used to form the expandable structures include, but are not limited to polypropylene, polyethylene, polybutylene terephthalate, Nylon 6, Nylon 11, polycarbonate, polyurethanes, polyesters, poly(vinylidenefluoride) and poly(ester-amides).

Once formed, the expanded member can be attached to an elongated catheter shaft by any conventional and suitable techniques so as to be in fluid communication with an inflation lumen. Similarly, the expandable member can be folded or collapsed using known and suitable techniques for assembly, packaging, delivery and deployment as is known in the art.

The following examples are presented in order to more fully illustrate certain embodiments of the invention. These examples in no way, however, should be construed as limiting the broad scope of the invention. One skilled in the art can readily devise many variations and modifications of the principles disclosed herein without departing from the scope of the invention.

EXAMPLES

Example A 2 wt % high inherent viscosity Poly(L-lactide) PLLA in hexafluoroisopropanol was electrospun utilizing voltages of +10 kV (nozzle) and −10 kV (mandrel), a flow rate of 1 mL/hr, over a distance of 10 cm onto a 4.0 mm stainless steel mandrel rotating at 3000 rpm. This PLLA fiber composite in the shape of a tube with a 4.0 mm inner diameter was then annealed at 45° C. overnight in a vacuum oven to remove residual solvent and induce crystallinity. A macroscale image of the foam conduit is shown in FIG. 8.

Example B

The PLLA electrospun tube segment formed in Example A was cut and placed on carbon tape, sputter coated with gold-palladium and then imaged by scanning electron microscopy. As shown in FIG. 9, surface morphology consists of micron and sub-micron diameter fibers layered on one another that include gaps therebetween.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. An intraluminal catheter device comprising:
an elongated catheter shaft having a proximal end portion and a distal end portion, the shaft having an inflation lumen disposed between the proximal end portion and the distal end portion; and
an expandable member formed essentially of an electrospun matrix of fiber elements and disposed proximate to the distal end portion of the catheter shaft to define an inner chamber fluidly coupled to the inflation lumen, individual fiber elements of the matrix coated with a hydrogel polymer coating having at least one therapeutic agent incorporated therein.

2. The device of claim 1, wherein the fiber elements comprise a polymer selected from the group consisting of polyamides, polyurethanes, fluoropolymers, polyolefins, polyimides, polyimines, (methyl)acrylic polymers, polyesters, and co-polymers thereof.

3. The device of claim 1, wherein the hydrogel polymer coating having the at least one therapeutic agent incorporated therein completely surrounds the individual fiber elements.

4. The device of claim 1, wherein the at least one therapeutic agent is selected from the group consisting of anti-proliferative, anti-inflammatory, antineoplastic, antiplatelet, anti-coagulant, anti-fibrin, antithrombotic, antimitotic, antibiotic, antiallergic and antioxidant compounds and combinations thereof.

5. The device of claim 1, wherein the individual fiber elements include a second coating surrounding the hydrogel polymer coating, the second coating comprising a protective substance.

6. The device of claim 5, wherein the protective substance is selected from the group consisting of glucose, hydrophilic coatings, mediums which are dissolvable in blood or aqueous mediums, and other mediums which will crack under expansion.

7. The device of claim 1, wherein the expandable member is expandable from a first profile to a second profile.

8. The device of claim 1, wherein the expandable member is essentially fluid-tight and can maintain an expanded profile.

9. The device of claim 1, the expandable member defining an outer surface, and further comprising a coating on at least one portion of the outer surface of the expandable member.

10. The device of claim 9, wherein the coating comprises a protective substance.

11. The device of claim 9, wherein the coating comprises a hydrogel polymer having at least one therapeutic agent incorporated therein.

12. The device of claim 11, further comprising a second coating surrounding the first coating on at least one portion of the outer surface of the expandable member, the second coating comprising a protective substance.

13. The device of claim 1, wherein the matrix of fiber elements defines a plurality of gaps between the fibers.

14. The device of claim 1, wherein the hydrogel polymer coating having the at least one therapeutic agent incorporated therein partially coats the individual fiber elements.

15. The device of claim 1, wherein the at least one therapeutic agent is released from the individual fiber elements upon radial expansion of the expandable member.

16. The device of claim 1, wherein the at least one therapeutic agent is released from the individual fiber elements by diffusion upon expansion of the expandable member against a target area.

17. The device of claim 1, wherein the at least one therapeutic agent is released from the individual fiber elements within five minutes after expansion of the expandable member.

18. An intraluminal catheter device made by:
forming an expandable member essentially of an electrospun matrix of fiber elements to define an inner chamber, individual fiber elements of the matrix carrying a hydrogel polymer coating having at least one therapeutic agent incorporated therein;

providing an elongated catheter shaft having a proximal end portion and a distal end portion, the shaft having an inflation lumen disposed between the proximal end portion and the distal end portion; and attaching the expandable member to the distal end portion of the elongated catheter shaft with the inner chamber of the expandable member fluidly coupled to the inflation lumen.

19. The device of claim 18, wherein the individual fiber elements include a second coating surrounding the hydrogel polymer coating, the second coating comprising a protective substance.

20. The device of claim 18, wherein the at least one therapeutic agent is released from the individual fiber elements upon radial expansion of the expandable member.

21. The device of claim 18, wherein the at least one therapeutic agent is released from the individual fiber elements by diffusion upon expansion of the expandable member against a target area.

22. The device of claim 18, wherein the at least one therapeutic agent is released from the individual fiber elements within five minutes after expansion of the expandable member.

* * * * *